United States Patent
Koseoglu et al.

(10) Patent No.: US 11,274,068 B2
(45) Date of Patent: *Mar. 15, 2022

(54) PROCESS FOR INTERCONVERSION OF OLEFINS WITH MODIFIED BETA ZEOLITE

(71) Applicants: Saudi Arabian Oil Company, Dhahran (SA); JGC Catalysts and Chemicals, Ltd., Kawasaki (JP); Japan Cooperation Center Petroleum, Tokyo (JP)

(72) Inventors: Omer Refa Koseoglu, Dhahran (SA); Robert Peter Hodgkins, Dhahran (SA); Mitsunori Watabe, Kanagawa (JP); Koji Uchida, Kanagawa (JP)

(73) Assignees: Saudi Arabian Oil Company, Dhahran (SA); JGC Catalysts and Chemicals Ltd., Saiwai-ku (JP); Japan Cooperation Center Petroleum, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/936,990

(22) Filed: Jul. 23, 2020

(65) Prior Publication Data

US 2022/0024839 A1 Jan. 27, 2022

(51) Int. Cl.
| | |
|---|---|
| C07C 6/04 | (2006.01) |
| B01J 29/70 | (2006.01) |
| B01J 29/08 | (2006.01) |
| B01J 29/80 | (2006.01) |
| B01J 35/10 | (2006.01) |
| C07C 5/05 | (2006.01) |
| B01J 29/04 | (2006.01) |
| B01J 29/06 | (2006.01) |
| B01J 29/89 | (2006.01) |
| B01J 29/00 | (2006.01) |
| B01J 37/00 | (2006.01) |
| C07C 5/02 | (2006.01) |
| C07C 5/03 | (2006.01) |

(52) U.S. Cl.
CPC .............. *C07C 6/04* (2013.01); *B01J 29/005* (2013.01); *B01J 29/041* (2013.01); *B01J 29/061* (2013.01); *B01J 29/084* (2013.01); *B01J 29/088* (2013.01); *B01J 29/7007* (2013.01); *B01J 29/7057* (2013.01); *B01J 29/80* (2013.01); *B01J 29/89* (2013.01); *B01J 35/109* (2013.01); *B01J 35/1019* (2013.01); *B01J 35/1023* (2013.01); *B01J 35/1038* (2013.01); *B01J 35/1042* (2013.01); *B01J 35/1057* (2013.01); *B01J 35/1061* (2013.01); *B01J 35/1066* (2013.01); *B01J 37/0009* (2013.01); *C07C 5/02* (2013.01); *C07C 5/03* (2013.01); *C07C 5/05* (2013.01); *B01J 2029/062* (2013.01); *B01J 2229/183* (2013.01); *B01J 2229/37* (2013.01); *B01J 2229/42* (2013.01); *C07C 2529/06* (2013.01); *C07C 2529/08* (2013.01); *C07C 2529/70* (2013.01); *C07C 2529/80* (2013.01); *C07C 2529/89* (2013.01)

(58) Field of Classification Search
CPC ...... B01J 29/084; B01J 29/041; B01J 29/061; B01J 29/088; B01J 29/7057; B01J 29/7007; B01J 29/80; B01J 29/89; B01J 29/005; B01J 2029/062; B01J 2229/183; B01J 2229/37; B01J 2229/42; B01J 35/1019; B01J 35/1023; B01J 35/1038; B01J 35/1057; B01J 35/109; B01J 35/1042; B01J 35/1061; B01J 35/1066; B01J 37/0009; C07C 6/04; C07C 5/02; C07C 5/03; C07C 5/05; C07C 2529/08; C07C 2529/06; C07C 2529/70; C07C 2529/80; C07C 2529/89
USPC ....... 585/250, 251, 252, 259, 260, 264, 265; 208/49, 57, 143, 144
See application file for complete search history.

(56) References Cited

U.S. PATENT DOCUMENTS

| | | | |
|---|---|---|---|
| 3,523,914 | A | 8/1970 | Mitsche et al. |
| 3,842,138 | A | 10/1974 | Chahvekilian et al. |

(Continued)

FOREIGN PATENT DOCUMENTS

| | | |
|---|---|---|
| CA | 2041905 A1 | 11/1991 |
| CN | 101134576 A | 3/2008 |

(Continued)

OTHER PUBLICATIONS

Machine translation of CN 106140289, Nov. 23, 2016.*

(Continued)

*Primary Examiner* — Elizabeth D Wood
(74) *Attorney, Agent, or Firm* — Dinsmore & Shohl, LLP

(57) ABSTRACT

Methods for interconverting olefins in an olefin-rich hydrocarbon stream include contacting the olefin-rich hydrocarbon stream with a catalyst system in an olefin interconversion unit to produce an interconverted effluent comprising ethylene and propylene. The contacting may be conducted at a reaction temperature from 450° C. to 750° C., a reaction pressure from 1 bar to 5 bar, and a residence time from 0.5 seconds to 1000 seconds. The catalyst system includes a framework-substituted beta zeolite. The framework-substituted beta zeolite has a *BEA aluminosilicate framework that has been modified by substituting a portion of framework aluminum atoms of the *BEA aluminosilicate framework with beta-zeolite Al-substitution atoms independently selected from the group consisting of titanium atoms, zirconium atoms, hafnium atoms, and combinations thereof.

19 Claims, No Drawings

(56) References Cited

U.S. PATENT DOCUMENTS

| | | |
|---|---|---|
| 3,944,481 A | 3/1976 | Wing et al. |
| 4,002,556 A | 1/1977 | Satchell |
| 4,065,379 A | 12/1977 | Soonawala et al. |
| 4,115,467 A | 9/1978 | Fowler |
| 4,180,453 A | 12/1979 | Franck et al. |
| 4,210,560 A | 7/1980 | Kehl |
| 4,255,288 A | 3/1981 | Cull et al. |
| 4,419,271 A | 12/1983 | Ward |
| 4,698,322 A | 10/1987 | Santilli et al. |
| 4,738,941 A | 4/1988 | Dufresne et al. |
| 4,798,665 A | 1/1989 | Humbach et al. |
| 4,826,586 A | 5/1989 | Herbst et al. |
| 4,859,308 A * | 8/1989 | Harandi ............... C10G 11/182 208/49 |
| 5,057,203 A | 10/1991 | Chu et al. |
| 5,185,484 A | 2/1993 | Del Rossi et al. |
| 5,192,421 A | 3/1993 | Audeh et al. |
| 5,258,117 A | 11/1993 | Kolstad et al. |
| 5,264,635 A * | 11/1993 | Le ............................ C07C 6/04 568/697 |
| 5,271,761 A | 12/1993 | Skeels et al. |
| 5,414,175 A | 5/1995 | Cook |
| 5,690,810 A | 11/1997 | Lawrence et al. |
| 5,906,728 A | 5/1999 | Iaccino et al. |
| 6,017,840 A | 1/2000 | Wu et al. |
| 6,063,944 A | 5/2000 | Di Renzo et al. |
| 6,132,494 A | 10/2000 | Tore et al. |
| 6,190,533 B1 | 2/2001 | Bradow et al. |
| 6,210,561 B1 | 4/2001 | Bradow et al. |
| 6,303,842 B1 | 10/2001 | Bridges et al. |
| 6,632,351 B1 | 10/2003 | Ngan et al. |
| 6,726,834 B2 | 4/2004 | Quesada et al. |
| 6,762,143 B2 | 7/2004 | Shan et al. |
| 7,084,087 B2 | 8/2006 | Shan et al. |
| 7,220,887 B2 | 5/2007 | Stell et al. |
| 7,331,746 B2 | 2/2008 | Wright et al. |
| 7,408,093 B2 | 8/2008 | Stell et al. |
| 7,550,405 B2 | 6/2009 | Shan et al. |
| 7,700,005 B2 | 4/2010 | Inui et al. |
| 7,951,745 B2 | 5/2011 | Zhou et al. |
| 7,972,498 B2 | 7/2011 | Buchanan et al. |
| 8,002,970 B2 | 8/2011 | Euzen et al. |
| 8,008,226 B2 | 8/2011 | Inui et al. |
| 8,070,938 B2 | 12/2011 | Stein et al. |
| 8,071,833 B2 | 12/2011 | Grootjans et al. |
| 8,148,285 B2 | 4/2012 | Kuroda et al. |
| 8,884,088 B2 | 11/2014 | Smith et al. |
| 9,108,190 B1 | 8/2015 | Fan et al. |
| 9,221,036 B2 | 12/2015 | Koseoglu et al. |
| 9,321,704 B2 | 4/2016 | Lattner et al. |
| 9,499,403 B2 | 11/2016 | Al-Muhaish et al. |
| 9,512,371 B2 | 12/2016 | Abe et al. |
| 9,879,187 B2 | 1/2018 | Bhan |
| 9,908,109 B2 | 3/2018 | Ravishankar et al. |
| 10,053,401 B1 | 8/2018 | Beadle et al. |
| 10,081,009 B2 | 9/2018 | Koseoglu et al. |
| 10,137,442 B2 | 11/2018 | McGuire |
| 10,293,332 B2 | 5/2019 | Koseoglu et al. |
| 10,350,585 B1 | 7/2019 | Al-Herz et al. |
| 10,427,142 B1 | 10/2019 | Al-Herz et al. |
| 10,494,574 B2 | 12/2019 | Akah et al. |
| 10,941,354 B1 | 3/2021 | Hodgkins et al. |
| 2003/0006168 A1 | 1/2003 | Ino et al. |
| 2004/0004028 A1 | 1/2004 | Stell et al. |
| 2004/0054247 A1 | 3/2004 | Powers |
| 2005/0209093 A1 | 9/2005 | Chester et al. |
| 2005/0232839 A1 | 10/2005 | Yaluris et al. |
| 2005/0261530 A1 | 11/2005 | Stell et al. |
| 2006/0021912 A1 | 2/2006 | Chen et al. |
| 2007/0090018 A1 | 4/2007 | Keusenkothen et al. |
| 2007/0090020 A1 | 4/2007 | Buchanan et al. |
| 2007/0232846 A1 | 10/2007 | Baumgartner et al. |
| 2009/0283443 A1 | 11/2009 | Kuroda et al. |
| 2010/0087692 A1 | 4/2010 | Yoshimura et al. |
| 2011/0042269 A1 | 2/2011 | Kuechler et al. |
| 2011/0132804 A1 | 6/2011 | Stevenson et al. |
| 2011/0174682 A1 | 7/2011 | Iaccino |
| 2011/0247500 A1 | 10/2011 | Akhras et al. |
| 2011/0251049 A1 | 10/2011 | Kuroda et al. |
| 2012/0085681 A1 | 4/2012 | Abe et al. |
| 2013/0046122 A1 | 2/2013 | Vermeiren et al. |
| 2013/0066131 A1 | 3/2013 | Harris |
| 2013/0175202 A1 | 7/2013 | Koseoglu et al. |
| 2013/0319910 A1 | 12/2013 | Koseoglu et al. |
| 2015/0111721 A1 | 4/2015 | Tian et al. |
| 2015/0111722 A1 | 4/2015 | Long et al. |
| 2015/0375218 A1 | 12/2015 | Koseoglu et al. |
| 2017/0088490 A1 * | 3/2017 | Chen ..................... B01J 21/18 |
| 2019/0093028 A1 | 3/2019 | Gong et al. |
| 2019/0316044 A1 | 10/2019 | Koseoglu et al. |
| 2020/0055025 A1 | 2/2020 | Kukade et al. |

FOREIGN PATENT DOCUMENTS

| | | |
|---|---|---|
| CN | 101898144 A | 12/2010 |
| CN | 104549543 A | 4/2015 |
| CN | 106140289 A | 11/2016 |
| CN | 106145136 A | 11/2016 |
| EP | 703003 A1 | 3/1996 |
| EP | 2298445 A1 | 3/2011 |
| EP | 3406337 A1 | 11/2018 |
| GB | 1255544 A | 12/1971 |
| GB | 2114594 A | 8/1983 |
| JP | 58098387 A | 6/1983 |
| JP | 07308581 A | 11/1995 |
| JP | 2000334305 A | 12/2000 |
| JP | 2002255537 A | 9/2002 |
| JP | 2003226519 A | 8/2003 |
| WO | 8801254 A1 | 2/1988 |
| WO | 0104237 A2 | 1/2001 |
| WO | 2007047942 A2 | 4/2007 |
| WO | 2009088413 A1 | 7/2009 |
| WO | 2012018819 A1 | 2/2012 |
| WO | 2013057319 A2 | 4/2013 |
| WO | 2013123299 A1 | 8/2013 |
| WO | 2015179735 A1 | 11/2015 |
| WO | 2019147345 A1 | 8/2019 |

OTHER PUBLICATIONS

International Search Report pertaining to Application No. PCT/US2015/032129 dated Aug. 21, 2015.
Wang et al., "Characterization of titanium-modified USY zeolites and their catalytic performance on n-heptane cracking", Appl Catal A-Gen, vol. 214, No. 2, pp. 167-177, Jun. 29, 2001.
International Search Report pertaining to Application No. PCT/US2013/023337 dated Jun. 18, 2013.
International Search Report pertaining to Application No. PCT/US2018/064001 dated Feb. 18, 2019.
Hamdy et al., "Structural and photocatalytic properties of precious metals modified TiO2-BEA Zeolite composites", Molecular Catalysis, vol. 441, pp. 140-149, 2017.
Rakshe et al., "Acidity and m-Xylene Isomerization Activity of Large Pore, Zirconium-Containing Alumino-silicate with BEA Structure", Journal of Catalysis, vol. 188, pp. 252-260, 1999.
Reddy et al., "A Simple Method for the Preparation of Active Ti Beta Zeolite Catalysts", Catalysisby Microporous Materials, Studies int eh Surface Science and Catalysis, vol. 94, pp. 309-316, 1995.
International Search Report and Written Opinion dated Mar. 31, 2021 pertaining to International application No. PCT/US2020/057484 filed Oct. 27, 2020, 14 pgs.
International Search Report and Written Opinion dated Apr. 9, 2021 pertaining to International application No. PCT/US2020/060860 filed Nov. 17, 2020, 12 pgs.
International Search Report and Written Opinion dated Apr. 13, 2021 pertaining to International application No. PCT/US2020/066520 filed Dec. 22, 2020, 12 pgs.
International Search Report and Written Opinion dated Apr. 21, 2021 pertaining to International application No. PCT/US2020/058208 filed Oct. 30, 2020, 12 pgs.

(56) References Cited

OTHER PUBLICATIONS

International Search Report and Written Opinion dated Mar. 17, 2021 pertaining to International application No. PCT/US2020/058682 filed Nov. 3, 2020, 16 pgs.
International Search Report and Written Opinion dated Sep. 10, 2021 pertaining to International application No. PCT/US2021/034220 filed May 26, 2021, 14 pages.
Sun, X. et al. "Synthesis of Zeolite β and Its Performance in Catalytic Cracking", Journal of Chemical Engineering of Japan, vol. 42, No. 10, Jan. 1, 2009, pp. 760-766.
U.S. Office Action dated Jul. 8, 2021 pertaining to U.S. Appl. No. 16/923,346, filed Jul. 8, 2020, 35 pages.
U.S. Notice of Allowance and Fee(s) Due dated Aug. 4, 2021 pertaining to U.S. Appl. No. 16/940,635, filed Jul. 28, 2020, 42 pages.
U.S. Office Action dated Aug. 6, 2021 pertaining to U.S. Appl. No. 16/940,711, filed Jul. 28, 2020, 40 pages.
Notice of Allowance and Fee(s) Due dated Jun. 9, 2021 pertaining to U.S. Appl. No. 16/985,588, filed Aug. 5, 2020, 35 pages.
U.S. Office Action dated Dec. 2, 2021 pertaining to U.S. Appl. No. 16/936,987, filed Jul. 23, 2020, 53 pages.

\* cited by examiner

PROCESS FOR INTERCONVERSION OF OLEFINS WITH MODIFIED BETA ZEOLITE

TECHNICAL FIELD

The present application relates to methods for processing hydrocarbon streams and, more particularly to methods for interconverting olefin-rich hydrocarbon streams to produce propylene and ethylene.

BACKGROUND

Selective olefin cracking technology is one of the processing routes to produce propylene. The feedstock for selective olefin cracking may include olefin-rich hydrocarbons with carbon numbers from 4 to 12 from cracking units such as steam pyrolysis and fluid catalytic cracking. Some methods for C4/C5 cracking are similar to metathesis in that low-value hydrocarbon streams are converted to higher value olefins. However, there are many differences between general C4/C5 cracking and selective olefin cracking. With selective C4/C5 cracking technologies, C5 streams can be converted along with the C4 stream, including isobutene. Normal butenes do not require isomerization. In addition, ethylene is not consumed in the process; in fact, additional ethylene is produced along with the main propylene product.

Efficiency and yield of selective olefin cracking depend heavily on the catalysts, and the catalyst systems including the catalysts, that drive the interconverted product stream to contain optimal proportions of high-value products such as propylene. Accordingly, ongoing needs remain for catalysts and catalyst systems that increase the yields of high-value products in selective olefin cracking processes.

SUMMARY

Against the foregoing background, example embodiments of this disclosure are directed to methods for interconverting olefins in an olefin-rich hydrocarbon stream. The methods include contacting the olefin-rich hydrocarbon stream with a catalyst system in an olefin interconversion unit to produce an interconverted effluent comprising ethylene and propylene. The contacting may be conducted at a reaction temperature from 450° C. to 750° C., a reaction pressure from 1 bar to 5 bar, and a residence time from 0.5 seconds to 1000 seconds. The catalyst system includes a framework-substituted beta zeolite. The framework-substituted beta zeolite has a *BEA aluminosilicate framework that has been modified by substituting a portion of framework aluminum atoms of the *BEA aluminosilicate framework with beta-zeolite Al-substitution atoms independently selected from the group consisting of titanium atoms, zirconium atoms, hafnium atoms, and combinations thereof.

According to some embodiments, the catalyst system further may include, in addition to the framework-substituted beta zeolite, a framework-substituted ultra-stable Y (USY) zeolite. In such embodiments, the framework-substituted USY-zeolite has a modified USY framework. The modified USY framework may be a USY aluminosilicate framework that has been modified by substituting a portion of framework aluminum atoms of the USY aluminosilicate framework with USY-zeolite Al-substitution atoms independently selected from the group consisting of titanium atoms, zirconium atoms, hafnium atoms, and combinations thereof.

Additional features and advantages of the embodiments described herein will be set forth in the detailed description that follows, and in part will be readily apparent to those skilled in the art from that description or recognized by practicing the embodiments described herein, including the detailed description and claims that follow. It is to be understood that both the foregoing general description and the following detailed description describe various embodiments and are intended to provide an overview or framework for understanding the nature and character of the claimed subject matter.

DETAILED DESCRIPTION

Embodiments of this disclosure are directed to olefin interconversion of olefin-rich hydrocarbon streams in the presence of a framework-substituted beta zeolite catalyst to produce a product stream containing propylene and ethylene. Olefin interconversion processes entail four primary reactions among olefinic compounds in a hydrocarbon stream. The four reactions include olefin oligomerization, cracking, disproportionation, and hydrogen transfer. The reactions may occur simultaneously within a single reactor to thereby interconvert a feed mixture of multiple olefin compounds into an interconverted mixture of other compounds. The composition of the interconverted mixture may include high-value products such as propylene and ethylene, for example, in greater or substantially greater amounts than present in the feed mixture.

During olefin oligomerization, olefins having X carbon atoms combine with olefins having Y carbon atoms, where X and Y are the same or different, to form olefins having X+Y carbon atoms. Cracking is essentially the reverse of olefin oligomerization, whereby olefin olefins having X+Y carbon atoms are cracked to form equimolar amounts of olefins having X carbon atoms and olefins having Y carbon atoms. Disproportionation refers to a reaction by which olefins having X carbon atoms and olefins having Y carbon atoms are converted to olefins having U carbon atoms and olefins having V carbon atoms, where X+Y=U+V. Hydrogen transfer reactions include conversions of olefins having the same or different carbon numbers to cyclo-olefins, alkanes (paraffins), cycloalkanes (naphthenes), aromatics, or combinations thereof. The catalyst and reaction conditions determine the ultimate distribution of products from interconversion. To maximize production of light olefins such as propylene, ethylene, or both, from an interconversion process, it is desirable to minimize particularly the hydrogen-transfer reactions and cyclization reactions that form alkanes and aromatic compounds.

Reference will now be made in detail to embodiments of methods for interconverting olefins in an olefin-rich hydrocarbon stream. The methods include contacting the olefin-rich hydrocarbon stream with a catalyst system in an olefin interconversion unit to produce an interconverted effluent containing ethylene and propylene. The contacting is conducted under reactor conditions that facilitate interconversion reactions. In embodiments, the contacting is conducted at a reaction temperature from 450° C. to 750° C., a reaction pressure from 1 bar to 5 bar, and a residence time from 0.5 seconds to 60 seconds. The catalyst system includes a framework-substituted beta zeolite having a modified *BEA framework. As will be described subsequently in greater detail, the modified *BEA framework is a *BEA aluminosilicate framework that has been modified by substituting a portion of framework aluminum atoms of the *BEA aluminosilicate framework with beta-zeolite Al-substitution atoms. The beta-zeolite Al-substitution atoms are independently selected from the group consisting of titanium atoms, zirconium atoms, and hafnium atoms.

The olefin-rich hydrocarbon streams according to embodiments may be selected from any refinery stream containing at least 20% by mass, at least 30% by mass, at least 40% by mass, at least 50% by mass, at least 60% by mass, at least 70% by mass, or at least 80% by mass olefins, based on the total mass of the hydrocarbon stream. As used herein, the term "olefins" with respect to the hydrocarbon stream includes linear or branched hydrocarbons containing at least one carbon-carbon double bond. The term "monoolefins" refers to hydrocarbons containing exactly one carbon-carbon double bond. The term "diolefins" refers to hydrocarbons containing exactly two carbon-carbon double bonds. The term "hydrocarbon" refers to linear, branched, cyclic, or aromatic compounds, each of any size or carbon-chain length, including only carbon and hydrogen atoms.

In specific example embodiments, the olefin-rich hydrocarbon stream may be chosen from a raw C4 refinery stream, a raffinate-1 stream, a raffinate-2 stream, a C4 stream from a fluid catalytic cracker, and a C5+ stream from cracker pyrolysis gasoline. In some embodiments, the olefin-rich hydrocarbon stream is an effluent from a steam pyrolysis unit or a fluidized catalytic cracking unit. In some embodiments, the olefin-rich hydrocarbon stream may include hydrocarbons having from 4 to 12 carbon atoms, or from 4 to 10 carbon atoms, or from 4 to 8 carbon atoms.

Raw C4 refinery streams may be products of vacuum distillation or other separation process from petroleum or crude oil. The raw C4 streams contain primarily C4 hydrocarbons that are a mixture of alkanes, and olefins, including monoolefins and diolefins. A raffinate-1 stream is a product of a raw C4 stream from which 1,3-butadiene (a diolefin) has been removed by separation. The raffinate-1 stream typically contains about 40% to about 50% by mass isobutylene and about 30% to about 35% by mass 2-butene isomers (cis-2-butene and trans-2-butene). A raffinate-2 stream is a product of a raw C4 stream from which 1,3-butadiene and isobutylene have been removed. The raffinate-2 stream typically contains about 50% to about 60% by mass 2-butene isomers, about 10% to about 15% by mass 1-butene, and about 20% by mass n-butane. The C5+ stream may contain at least 50% by mass hydrocarbons having greater than five carbon atoms. In some embodiments, the C5+ stream may contain greater than 90% by mass hydrocarbons having from 6 to 10 carbon atoms. It should be understood that the olefin-rich hydrocarbon stream according to embodiments is not limited to any specific composition, provided the olefins in the olefin-rich hydrocarbon stream are of sufficient amount to undergo the interconversion reactions as previously described under the chosen reactor conditions in the presence of the catalyst system.

In the olefin interconversion processes according to embodiments, the olefin-rich hydrocarbon stream may be derived from one or more of crude oil, synthetic crude oil, bitumen, oil sand, shale oil and coal liquid. The olefin-rich hydrocarbon stream may include petroleum fractions having a normal point greater than 350° C., including naphtha, diesel, vacuum gas oil (VGO), deasphalted oil (DAO) obtained from a solvent deasphalting process, demetallized oil, light or heavy coker gas oil obtained from a coker process, cycle oil obtained from a separate fluidized catalytic cracking (FCC) process or recycled from an FCC process, gas oil obtained from a visbreaking process, or combinations comprising at least one of the foregoing.

In embodiments of the methods for interconverting olefins in an olefin-rich hydrocarbon stream, the olefin-rich hydrocarbon stream is contacted with a catalyst system in an olefin interconversion unit to produce an interconverted effluent containing ethylene and propylene. The catalyst system will now be described in detail. The interconversion unit and suitable reaction conditions and parameters will be described thereafter.

Framework-Substituted Beta Zeolite Catalyst

In embodiments of methods for interconverting olefins in an olefin-rich hydrocarbon stream, the catalyst system with which the olefin-rich hydrocarbon stream is contacted includes a catalyst. The catalyst includes a framework-substituted beta zeolite. The framework-substituted beta zeolite has a modified *BEA framework.

The modified *BEA framework is an analog to a *BEA aluminosilicate framework according to the standard definition of a *BEA aluminosilicate framework. According to the standard definition, a *BEA aluminosilicate framework is a crystalline aluminosilicate zeolite having a crystal lattice constants a and b (UD) from 1.26 nm to 1.27 nm, a unit cell length c from 2.62 nm to 2.65 nm, a specific surface area of 400 $m^2/g$ to 800 $m^2/g$, and a molar ratio of silicon to aluminum from 10 to 200, as calculated on the basis of silica ($SiO_2$) and alumina ($Al_2O_3$).

With regard to the framework-substituted *BEA-type zeolite according to embodiments of this disclosure, the modified *BEA aluminosilicate framework is a *BEA aluminosilicate framework modified by substituting a portion of framework aluminum atoms of the *BEA aluminosilicate framework with beta-zeolite Al-substitution atoms independently selected from the group consisting of titanium atoms, zirconium atoms, and hafnium atoms, and combinations thereof.

As used in this disclosure, the term "Ti-*BEA" refers to a framework-substituted *BEA-type zeolite according to embodiments, in which the substitution atoms are titanium. Likewise, the term "Zr-*BEA" refers to a framework-substituted *BEA-type zeolite according to embodiments, in which the beta-zeolite Al-substitution atoms include zirconium. The term "Hf-*BEA" refers to a framework-substituted *BEA-type zeolite according to embodiments, in which the beta-zeolite Al-substitution atoms include hafnium. The term "(Ti,Zr)-*BEA" refers to a framework-substituted *BEA-type zeolite according to embodiments, in which the beta-zeolite Al-substitution atoms include titanium and zirconium. The term "(Ti,Hf)-*BEA" refers to a framework-substituted *BEA-type zeolite according to embodiments, in which the beta-zeolite Al-substitution atoms include titanium and hafnium. The term "(Zr,Hf)-*BEA" refers to a framework-substituted *BEA-type zeolite according to embodiments, in which the beta-zeolite Al-substitution atoms include zirconium and hafnium. The term "(Ti,Zr,Hf)-*BEA" refers to a framework-substituted *BEA-type zeolite according to embodiments, in which the beta-zeolite Al-substitution atoms include titanium, zirconium, and hafnium.

The framework-substituted *BEA-type zeolite according to embodiments may be Ti-*BEA, Zr-*BEA, Hf-*BEA, (Ti,Zr)-*BEA, (Ti,Hf)-*BEA, (Zr,Hf)-*BEA, or (Ti,Zr,Hf)-*BEA, as previously defined. The beta-zeolite Al-substitution atoms are substituted for the aluminum atoms forming a framework of the *BEA-type zeolite and, therefore, serve as constituents of the framework of the *BEA-type zeolite. Substitution can be verified by analytical techniques including, but not limited to, ultraviolet, visible, and near-infrared spectrophotometry (UV-Vis-NIR), Fourier-transform infrared spectroscopy (FT-IR), or nuclear magnetic resonance spectrometry (NMR).

In some embodiments, the framework-substituted *BEA-type zeolite includes from 0.01% to 5% by mass, or from 0.1% to 5% by mass, or from 0.2% to 4% by mass, or from 0.3% to 3% by mass beta-zeolite Al-substitution atoms, calculated on an oxide basis, based on the total mass of the framework-substituted *BEA-type zeolite. In calculations on oxide basis, titanium atoms are calculated on the basis of $TiO_2$, zirconium atoms are calculated on the basis of $ZrO_2$, and hafnium atoms are calculated on the basis of $HfO_2$. Titanium, zirconium, and hafnium in the framework-substituted *BEA-type zeolites may be quantitatively determined by known techniques, such as by X-ray fluorescence analysis, high-frequency plasma emission spectrometry, or atomic absorption spectrometry, for example.

In some embodiments, in addition to the aluminum-framework-substituted beta-zeolite Al-substitution atoms, the framework-substituted *BEA-type zeolite may further include zirconium atoms, titanium atoms, hafnium atoms, or any combination thereof, attached to, or carried on the outside of, or combined with the framework of the framework-substituted *BEA-type zeolite. In such embodiments, the zirconium, titanium, or hafnium atoms may be attached as oxide particles such as titania particles, zirconia particles, or hafnia particles. The oxide particles may have particle diameters of 50 nm or less. For the purpose of facilitating quantitative analysis, as contemplated herein, the amounts by mass of substitution atoms in the framework-substituted *BEA-type zeolite includes the total amount of titanium, zirconium, and hafnium, calculated on an oxide basis and based on the total mass of the framework-substituted *BEA-type zeolite that is either substituted for framework aluminum atoms or attached to, or carried on the outside of, or combined with the zeolite framework. It should be understood, however, that in all embodiments, at least a portion of the framework aluminum atoms of the *BEA aluminosilicate framework are substituted with titanium atoms, zirconium atoms, hafnium atoms, or any combination thereof. In example embodiments, greater than 50%, or greater than 75%, or greater than 90%, or greater than 99% of the titanium, zirconium, and hafnium atoms present in the framework-substituted *BEA-type zeolite are substituted for framework aluminum atoms in the zeolite framework and are not merely attached to, or carried on the outside of, or combined with the zeolite framework, particularly as particles.

It should be appreciated by a person of skill in the art, that when the framework-substituted *BEA-type zeolite contains a combination of beta-zeolite Al-substitution atoms, as in (Ti,Zr)-*BEA, (Ti,Hf)-*BEA, (Zr,Hf)-*BEA, or (Ti,Zr,Hf)-*BEA, the mass ratios of the individual types of beta-zeolite Al-substitution atoms in each zeolite, as calculated on an oxide basis, is not restricted. Though the reactions described in the methods according to embodiments may be tuned by adjusting ratios of titanium to zirconium to hafnium, it should be understood that any ratio of titanium to zirconium to hafnium may be effective to carry out the methods for cracking a hydrocarbon oil according to this disclosure.

The framework-substituted *BEA-type zeolite in the catalyst system may be prepared by any zeolite preparation method that results in a framework-substituted *BEA-type zeolite that has a *BEA aluminosilicate framework in which a part of framework aluminum atoms are substituted with titanium atoms, zirconium atoms, hafnium atoms, or any combination thereof. In one example preparation technique, the framework-substituted *BEA-type zeolite in the catalyst system is produced by firing a *BEA-type zeolite at 500° C. to 700° C., the *BEA-type zeolite having a crystal lattice constants a and b from 1.260 nm to 1.270 nm, a unit-cell length c from 2.62 nm to 2.65 nm, a specific surface area of 400 m²/g to 800 m²/g, and a molar ratio of silica to alumina of 10 to 200, or from 10 to 100, or from 30 to 70. Then, a suspension is formed containing the fired *BEA-type zeolite. The suspension may have a liquid/solid mass ratio of 5 to 15, based on the liquids and solids present in the suspension. An inorganic acid or an organic acid is added to the suspension to decrease the pH of the suspension to less than 2.0. The pH of the suspension is controlled in advance to less than 2.0 to prevent precipitation during mixing of one or more additional solution. Specifically, one or more additional solutions containing a compound of zirconium, titanium, hafnium, or combinations thereof is mixed into the suspension to cause framework substitution at aluminum sites. The suspension then is neutralized with a base such as aqueous ammonia, for example, to increase the pH to a range from 7 to 7.5. The resulting framework-substituted *BEA-type zeolite may be filtered, washed with water, and dried at a drying temperature from 80° C. to 180° C., for example.

In one specific and non-limiting example preparation of a (Ti,Zr)-*BEA framework-substituted *BEA-type zeolite according to embodiments, 51.4 g of a zeolite having a *BEA framework with a silica to alumina ratio of 28.5 is suspended in 450 g of deionized water, and heated to 40° C. Then, 14.8 g of $H_2SO_4$ (25 wt. %) is added, together with 10.0 g of an aqueous solution of titanium sulfate (equivalent to 5 wt. % $TiO_2$), to produce a solution containing 8.48 g deionized water and 1.52 g titanium sulfate (equivalent to 33 wt. % $TiO_2$). To the solution is added an additional aqueous zirconium sulfate solution (2.8 g, constituting 18 wt. % $ZrO_2$). The mixture is stirred for 4 hours at 60° C., then filtered and washed with 1.5 liters of deionized water. The resulting zeolite is dried at 110° C. to yield a framework substituted zeolite (Ti,Zr)-*BEA.

In the preparation of the framework-substituted *BEA-type zeolite, when mixing an aqueous solution of the zirconium compound, the hafnium compound, or the titanium compound with the suspension of the *BEA-type zeolite, the aqueous solution may be gradually added to the suspension. After the addition of the aqueous solution to the suspension is completed, the solution may be mixed by stirring at, for example, room temperature (25° C.±10° C.) for 3 hours to 5 hours. Further, after the mixing is completed, the mixed solution described above is neutralized by adding an alkali such as aqueous ammonia so that a pH thereof is controlled to 7.0 to 7.5, whereby the framework-substituted zeolite in the catalyst can be obtained.

In the preparation of the framework-substituted *BEA-type zeolite, the *BEA-type zeolite raw material may be calcined at 500° C. to 700° C. or 550° C. to 650° C. The calcining time is not specifically limited, as long as the framework-substituted *BEA-type zeolite is obtained. Example calcining times may be from 30 minutes to 10 hours. In respect to a calcining atmosphere of the *BEA-type zeolite raw material, it is carried out preferably in the air. The calcined *BEA-type zeolite raw material is suspended in water having a temperature of from 20° C. to 30° C. to form a suspension. With respect to the concentration of the suspension of the *BEA-type zeolite, the liquid/solid mass ratio may be from 5 to 15, or from 8 to 12, for example.

Non-limiting examples of inorganic acids for decreasing the pH of the suspension in the preparation of the framework-substituted *BEA-type zeolite may include sulfuric acid, nitric acid, or hydrochloric acid. Examples of organic acids for decreasing the pH of the suspension in the preparation of the framework-substituted *BEA-type zeolite may include carboxylic acids. Amounts of the inorganic acid or the organic acid are not limited, as long as a pH of the suspension can be controlled to a range of less than 2.0. Non-limiting example amounts of acid include molar amounts of acid from 0.5 to 4.0 times, or from 0.7 to 3.5 times the molar amount of alumina in the framework-substituted *BEA-type zeolite.

Non-limiting examples of the titanium compound present in the additional solution mixed into the suspension during preparation of the framework-substituted *BEA-type zeolite include titanium sulfate, titanium acetate, titanium chloride, titanium nitrate, titanium lactate, and any compound of titanium having sufficient solubility in the suspension to cause titanium atoms to replace aluminum atoms in the zeolite framework. In embodiments, an aqueous solution of a titanium compound prepared by dissolving the titanium compound in water is suitably used as the titanium compound.

Non-limiting examples of the zirconium compound present in the additional solution mixed into the suspension during preparation of the framework-substituted *BEA-type zeolite include zirconium sulfate, zirconium nitrate, zirconium chloride, and any compound of zirconium having sufficient solubility in the suspension to cause zirconium atoms to replace aluminum atoms in the zeolite framework. In embodiments, an aqueous solution of a zirconium compound prepared by dissolving the zirconium compound in water is suitably used as the zirconium compound.

Non-limiting examples of the hafnium compound present in the additional solution mixed into the suspension during preparation of the framework-substituted *BEA-type zeolite include hafnium chloride, hafnium nitrate, hafnium fluoride, hafnium bromide, hafnium oxalate, and any compound of hafnium having sufficient solubility in the suspension to cause hafnium atoms to replace aluminum atoms in the zeolite framework. In embodiments, an aqueous solution of a hafnium compound prepared by dissolving the hafnium compound in water is suitably used as the hafnium compound.

According to embodiments, the framework-substituted *BEA-type zeolite catalyst may have (a) a specific surface area of 400 $m^2/g$ to 800 $m^2/g$; (b) a molar ratio of $SiO_2$ to $Al_2O_3$ from 10 to 200; (c) a pore volume from 0.2 $cm^3/g$ to 0.6 $cm^3/g$; and (d) crystal lattice constants a=1.26 nm to 1.27 nm, b=1.26 nm to 1.27 nm, and c=2.62 to 2.65 nm. The framework-substituted *BEA-type zeolite catalyst may have a volume of pores having a diameter of 600 angstroms or less (60 nm or less) from 0.40 mL/g to 0.75 mL/g. In a non-limiting example embodiment, the framework-substituted *BEA-type zeolite catalyst additive may include a (Ti,Zr)-*BEA zeolite having (a) a specific surface area of 400 $m^2/g$ to 800 $m^2/g$; (b) a molar ratio of $SiO_2$ to $Al_2O_3$ of about 60; (c) a pore volume from 0.38 $cm^3/g$ to 0.43 $cm^3/g$; and (d) crystal lattice constants a=1.26 nm to 1.27 nm, b=1.26 nm to 1.27 nm, and c=2.62 to 2.65 nm. The framework-substituted *BEA-type zeolite catalyst may have mesopores having diameters from 4 nm to 100 nm.

In non-limiting example embodiments of the methods for cracking a hydrocarbon oil, the catalyst is a (Ti,Zr)-*BEA framework-substituted beta zeolite containing from 0.01% to 5% by mass beta-zeolite Al-substitution atoms, as calculated on an oxide basis, based on the total mass of the framework-substituted beta zeolite. In such example embodiments, the beta-zeolite Al-substitution atoms include titanium atoms and zirconium atoms.

According to embodiments, the catalyst system may include from 2% to 90% by mass, or from 5% to 90% by mass, or from 10% to 90% by mass, or from 20% to 70% by mass framework-substituted *BEA-type zeolite catalyst, based on the total mass of the catalyst system. Additional components of that optionally may be included in the catalyst system will be described in greater detail.

Optional Additional Components of Catalyst System

In embodiments of the methods for interconverting olefins in an olefin-rich hydrocarbon stream, the catalyst system optionally may include one or more ingredients in addition to the framework-substituted beta zeolite. Examples of such ingredients include, without limitation, one or more additional catalyst such as an additional zeolite catalyst, a catalyst matrix support, a binder, a filler, or an active metal component.

According to some embodiments, the catalyst system may include, in addition to the framework-substituted beta zeolite, an additional catalyst. Examples of additional catalysts include, without limitation, shape-selective zeolites having a pore diameter different from that of *BEA-type zeolite and thereby selective to permitting hydrocarbons with only limited shapes to enter the zeolite through its pores. Examples of suitable shape-selective zeolite components include, without limitation, zeolite Y, ultra-stable Y-type zeolite (USY zeolite), framework-substituted USY zeolite, ZSM-5 zeolite, zeolite omega, SAPO-5 zeolite, SAPO-11 zeolite, SAPO34 zeolite, and pentasil-type aluminosilicates, for example. When present in the catalyst system, the content of the additional shape-selective zeolite in the catalyst system may be from about 0.01% to 20% by mass, or from about 0.01% to 10% by mass, based on the total mass of the catalyst system.

In some embodiments, the catalyst system includes an additional catalyst and the additional catalyst includes a framework-substituted ultra-stable Y (USY)-zeolite. A framework-substituted ultra-stable Y (USY)-type zeolite according to embodiments has a modified USY framework. The modified USY framework is an analog to a USY aluminosilicate framework according to the standard definition of a USY aluminosilicate framework. According to the standard definition, USY aluminosilicate framework is that of an aluminosilicate zeolite having a crystal lattice constant (UD) of 2.430 nm or more and 2.450 nm or less, a specific surface area of 600 $m^2/g$ to 900 $m^2/g$, and a molar ratio of silicon to aluminum from 20 to 100, as calculated on the basis of silica ($SiO_2$) and alumina ($Al_2O_3$).

With regard to the framework-substituted USY-type zeolite according to embodiments of this disclosure, the modified USY framework is a USY aluminosilicate framework modified by substituting a portion of framework aluminum atoms of the USY aluminosilicate framework with USY-zeolite Al-substitution atoms. In embodiments, the USY-zeolite Al-substitution atoms are independently selected from the group consisting of titanium atoms, zirconium atoms, hafnium atoms, and combinations thereof.

As used in this disclosure, the term "Ti-USY" refers to a framework-substituted USY-type zeolite according to embodiments, in which the substitution atoms are titanium. Likewise, the term "Zr-USY" refers to a framework-substituted USY-type zeolite according to embodiments, in which the USY-zeolite Al-substitution atoms include zirconium. The term "Hf-USY" refers to a framework-substituted USY-type zeolite according to embodiments, in which the USY-zeolite Al-substitution atoms include hafnium. The term "(Ti,Zr)-USY" refers to a framework-substituted USY-type zeolite according to embodiments, in which the USY-zeolite Al-substitution atoms include titanium and zirconium. The term "(Ti,Hf)-USY" refers to a framework-substituted USY-type zeolite according to embodiments, in which the USY-zeolite Al-substitution atoms include titanium and hafnium.

The term "(Zr,Hf)-USY" refers to a framework-substituted USY-type zeolite according to embodiments, in which the USY-zeolite Al-substitution atoms include zirconium and hafnium. The term "(Ti,Zr,Hf)-USY" refers to a framework-substituted USY-type zeolite according to embodiments, in which the USY-zeolite Al-substitution atoms include titanium, zirconium, and hafnium.

The framework-substituted USY-type zeolite according to embodiments may be Ti-USY, Zr-USY, Hf-USY, (Ti,Zr)-USY, (Ti,Hf)-USY, (Zr,Hf)-USY, or (Ti,Zr,Hf)-USY, as previously defined. The USY-zeolite Al-substitution atoms are substituted for the aluminum atoms forming a framework of the ultra-stable Y-type zeolite and, therefore, serve as constituents of the framework of the ultra-stable Y-type zeolite. Substitution can be verified by analytical techniques including, but not limited to, ultraviolet, visible, and near-infrared spectrophotometry (UV-Vis-NIR), Fourier-transform infrared spectroscopy (FT-IR), or nuclear magnetic resonance spectrometry (NMR).

In some embodiments, the framework-substituted USY-type zeolite includes from 0.01% to 5% by mass, or from 0.1% to 5% by mass, or from 0.2% to 4% by mass, or from 0.3% to 3% by mass USY-zeolite Al-substitution atoms, calculated on an oxide basis, based on the total mass of the framework-substituted USY-type zeolite. In calculations on oxide basis, titanium atoms are calculated on the basis of $TiO_2$, zirconium atoms are calculated on the basis of $ZrO_2$, and hafnium atoms are calculated on the basis of $HfO_2$. Titanium, zirconium, and hafnium in the framework-substituted USY-type zeolites may be quantitatively determined by known techniques, such as by X-ray fluorescence analysis, high-frequency plasma emission spectrometry, or atomic absorption spectrometry, for example.

In some embodiments, in addition to the aluminum-framework-substituted substitution atoms, the framework-substituted USY-type zeolite may further include zirconium atoms, titanium atoms, hafnium atoms, or any combination thereof, attached to, or carried on the outside of, or combined with the framework of the framework-substituted USY-type zeolite. In such embodiments, the zirconium, titanium, or hafnium atoms may be attached as oxide particles such as titania particles, zirconia particles, or hafnia particles. The oxide particles may have particle diameters of 50 nm or less. For the purpose of facilitating quantitative analysis, as contemplated herein, the amounts by mass of substitution atoms in the framework-substituted USY-type zeolite includes the total amount of titanium, zirconium, and hafnium, calculated on an oxide basis and based on the total mass of the framework-substituted USY-type zeolite that is either substituted for framework aluminum atoms or attached to, or carried on the outside of, or combined with the zeolite framework. It should be understood, however, that in all embodiments, at least a portion of the framework aluminum atoms of the USY aluminosilicate framework are substituted with titanium atoms, zirconium atoms, hafnium atoms, or any combination thereof. In example embodiments, greater than 50%, or greater than 75%, or greater than 90%, or greater than 99% of the titanium, zirconium, and hafnium atoms present in the framework-substituted USY-type zeolite are substituted for framework aluminum atoms in the zeolite framework and are not merely attached to, or carried on the outside of, or combined with the zeolite framework, particularly as particles.

It should be appreciated by a person of skill in the art, that when the framework-substituted USY-type zeolite contains a combination of USY-zeolite Al-substitution atoms, as in (Ti,Zr)-USY, (Ti,Hf)-USY, (Zr,Hf)-USY, or (Ti,Zr,Hf)-USY, the mass ratios of the individual types of USY-zeolite Al-substitution atoms in each zeolite, as calculated on an oxide basis, is not restricted. Though the reactions described in the methods according to embodiments may be tuned by adjusting ratios of titanium to zirconium to hafnium, it should be understood that any ratio of titanium to zirconium to hafnium may be effective to carry out the methods for interconverting olefins according to this disclosure.

The framework-substituted USY-type zeolite in the catalyst system may be prepared by any zeolite preparation method that results in a framework-substituted USY-type zeolite that has a USY aluminosilicate framework in which a part of framework aluminum atoms are substituted with titanium atoms, zirconium atoms, hafnium atoms, or any combination thereof. In one example preparation technique, the framework-substituted USY-type zeolite in the catalyst system may be produced by firing a USY-type zeolite at 500° C. to 700° C., the USY-type zeolite having a crystal lattice constant of 2.430 nm to 2.450 nm, a specific surface area of 600 $m^2$/g to 900 $m^2$/g, and a molar ratio of silica to alumina of 20 to 100. Then, a suspension is formed containing the fired USY-type zeolite. The suspension may have a liquid/solid mass ratio of 5 to 15. An inorganic acid or an organic acid is added to the suspension to decrease the pH of the suspension to less than 2.0. The pH of the suspension is controlled in advance to less than 2.0 to prevent precipitation during mixing of one or more additional solution. Specifically, one or more additional solutions containing a compound of zirconium, titanium, hafnium, or combinations thereof is mixed into the suspension to cause framework substitution at aluminum sites. The suspension then is neutralized with a base such as aqueous ammonia, for example, to increase the pH to a range from 7 to 7.5. The resulting framework-substituted USY-type zeolite may be filtered, washed with water, and dried at a drying temperature from 80° C. to 180° C., for example.

In the preparation of the framework-substituted USY-type zeolite, the ultra-stable Y-type zeolite raw material may be calcined at 500° C. to 700° C. or 550° C. to 650° C. The calcining time is not specifically limited, as long as the framework-substituted USY-type zeolite is obtained. Example calcining times may be from 30 minutes to 10 hours. In respect to a calcining atmosphere of the USY-type zeolite raw material, it is carried out preferably in the air. The calcined USY-type zeolite raw material is suspended in water having a temperature of from 20° C. to 30° C. to form a suspension. With respect to the concentration of the suspension of the USY-type zeolite, the liquid/solid mass ratio may be from 5 to 15, or from 8 to 12, for example.

Non-limiting examples of inorganic acids for decreasing the pH of the suspension in the preparation of the framework-substituted USY-type zeolite may include sulfuric acid, nitric acid, or hydrochloric acid. Examples of organic acids for decreasing the pH of the suspension in the preparation of the framework-substituted USY-type zeolite may include carboxylic acids. Amounts of the inorganic acid or the organic acid are not limited, as long as a pH of the suspension can be controlled to a range of less than 2.0. Non-limiting example amounts of acid include molar amounts of acid from 0.5 to 4.0 times, or from 0.7 to 3.5 times the molar amount of alumina in the framework-substituted USY-type zeolite.

Non-limiting examples of the titanium compound present in the additional solution mixed into the suspension during preparation of the framework-substituted USY-type zeolite include titanium sulfate, titanium acetate, titanium chloride, titanium nitrate, titanium lactate, and any compound of titanium having sufficient solubility in the suspension to cause titanium atoms to replace aluminum atoms in the zeolite framework. In embodiments, an aqueous solution of a titanium compound prepared by dissolving the titanium compound in water is suitably used as the titanium compound.

Non-limiting examples of the zirconium compound present in the additional solution mixed into the suspension during preparation of the framework-substituted USY-type zeolite include zirconium sulfate, zirconium nitrate, zirconium chloride, and any compound of zirconium having sufficient solubility in the suspension to cause zirconium atoms to replace aluminum atoms in the zeolite framework. In embodiments, an aqueous solution of a zirconium compound prepared by dissolving the zirconium compound in water is suitably used as the zirconium compound.

Non-limiting examples of the hafnium compound present in the additional solution mixed into the suspension during preparation of the framework-substituted USY-type zeolite include hafnium chloride, hafnium nitrate, hafnium fluoride, hafnium bromide, hafnium oxalate, and any compound of hafnium having sufficient solubility in the suspension to cause hafnium atoms to replace aluminum atoms in the zeolite framework. In embodiments, an aqueous solution of a hafnium compound prepared by dissolving the hafnium compound in water is suitably used as the hafnium compound.

In the preparation of the framework-substituted USY-type zeolite, when mixing an aqueous solution of the zirconium compound, the hafnium compound, or the titanium compound with the suspension of the ultra-stable Y-type zeolite, the aqueous solution may be gradually added to the suspension. After the addition of the aqueous solution to the suspension is completed, the solution may be mixed by stirring at, for example, room temperature (25° C.±10° C.) for 3 hours to 5 hours. Further, after the mixing is completed, the mixed solution described above is neutralized by adding an alkali such as aqueous ammonia so that a pH thereof is controlled to 7.0 to 7.5, whereby the framework-substituted zeolite in the catalyst can be obtained.

The catalyst system of the methods according to embodiments may further include a support for the catalysts, particularly for the framework-substituted *BEA-type zeolite catalyst and any additional catalysts that optionally may be present. In some embodiments, the support may include an inorganic oxide excluding the framework-substituted *BEA-type zeolite catalyst. The inorganic oxide of the support may further include a substance serving as a granulating agent or a binder. Any substance that is contained in any known zeolite catalyst support including as a granulating agent may be used. Examples of such inorganic oxides include, but are not limited to alumina, silica, titania, silica-alumina, alumina-titania, alumina-zirconia, alumina-boria, phosphorus-alumina, silica-alumina-boria, phosphorus-alumina-boria, phosphorus-alumina-silica, silica-alumina-titania, and silica-alumina-zirconia. In example embodiments, the catalyst system includes as a support an inorganic oxide chosen from alumina and silica-alumina. Silica-alumina supports may be amorphous.

In embodiments for which the catalyst system includes a support, the mass ratios of the zeolites and the support may vary according to the desired level of catalyst activity. In example embodiments, the catalyst system may include from 2% to 80% by mass, from 10% to 80% by mass, or from 20% to about 70% by mass zeolites based on the total mass of the catalyst system. Likewise, the catalyst system may include a catalyst support composing from 20% to 98% by mass, or from 20% to 90% by mass, or from 30% to 80% by mass, based on the total mass of the catalyst system.

In further example embodiments, the catalyst system may include a binder such as a silica-based binder or an alumina-based binder. The silica based binder and alumina based binder can be used as inorganic binder. The silica based binder can be any one of or two or more of silica sol, water glass (sodium silicate), and silicic acid liquid. For example, silica sol comprising $SiO_2$ at a concentration in the range of 10% to 15% by mass can be prepared by adding water glass comprising $SiO_2$ at a concentration in the range of 12% to 23% by mass and sulfuric acid having a concentration in the range of 20% to 30% by mass simultaneously and continuously. Aluminum-compound binder can be (a) basic aluminum chloride, (b) aluminum biphosphate, or (c) alumina sol. A solution obtained by dissolving any kind of or two or more kinds of crystallite alumina, such as gibbsite, bayerrite, and boehmite, in an acid solution may be used as the aluminum-compound binder instead. Here, basic aluminum chloride is expressed as $[Al_2(OH)_nCl_{6-n}]_m$, where n is an integer and m is a natural number, and where 0<n<6 and 1<m<10, or, in some embodiments, where 4.8<n<5.3 and 3<m<7.

The catalyst system of the methods according to embodiments may further include active metal components selected from individual metals or combinations of metals from IUPAC Groups 7 to 11 of the Periodic Table. Examples of active metals include iron, cobalt, nickel, rhodium, palladium, silver, iridium, platinum, gold, chromium, molybdenum, and tungsten. Non-limiting examples of combinations of metal components include combinations of molybdenum and tungsten; combinations of cobalt and nickel; and combinations of any one or more of molybdenum, tungsten, cobalt, or nickel with a platinum-group metal such as platinum, rhodium, or palladium. In example embodiments, the catalyst system may include at least one active-phase metal chosen from nickel, molybdenum, tungsten, platinum, palladium, and combinations thereof.

When a metal component is included in the catalyst system, the catalyst system may contain from greater than zero to about 40% by mass metal component, calculated on an oxide basis for oxide components or on a metal basis for metals, based on the total mass of the catalyst system. In example embodiments, the catalyst system may include from 3% to 30% by mass of a metal component such as molybdenum, tungsten, cobalt, or nickel, calculated on an oxide basis, based on the total mass of the catalyst system. In further example embodiments, the catalyst system may include from 0.01% to 2% by mass of a metal component chosen from platinum, rhodium, or palladium, calculated on a metal basis, based on the total mass of the catalyst system.

In non-limiting example embodiments, in the methods for interconverting olefins in an olefin-rich hydrocarbon stream, the catalyst system may include the framework-substituted *BEA-type zeolite catalyst, at least one additional zeolite catalyst or catalyst additive, a catalyst matrix support, a binder, and a filler. In such example embodiments, the catalyst matrix support may include alumina or silica-alumina; the binder may be a sol of a porous inorganic oxide selected from the group consisting of alumina, silica, boria, chromia, magnesia, zirconia, titania, silica-alumina, and combinations thereof; and the filler may be a clay selected from the group consisting of kaolin, montmorillonite, halloysite, bentonite, and combinations thereof. In a non-limiting example, the catalyst system may include, based on the total mass of the catalyst system: from 1% to 50% by mass framework-substituted *BEA-type zeolite catalyst; from 1% to 50% by mass additional zeolite catalyst; from 0.1% to 15% by mass binder; and from 0.1% to 15% by mass clay. In a further non-limiting example, the catalyst system may include, based on the total mass of the catalyst system: from 1% to 50% by mass framework-substituted *BEA-type zeolite catalyst; from 1% to 50% by mass framework-substituted *USY-type zeolite catalyst; from 0.1% to 15% by mass binder; and from 0.1% to 15% by mass clay.

Having now described the catalyst system in detail, embodiments of the interconversion process and apparatus involved will now be described.

Interconversion Process

As previously described, the methods for interconverting olefins in an olefin-rich hydrocarbon stream include contacting the olefin-rich hydrocarbon stream with the catalyst system in an olefin interconversion unit to produce an interconverted effluent containing ethylene and propylene. Example embodiments of the olefin-rich hydrocarbon stream and the catalyst system have been described in detail. The interconversion process parameters and apparatus will now be described.

According to embodiments, the contacting the olefin-rich hydrocarbon stream with the catalyst system may be accomplished by any suitable method, based on the configuration of the olefin interconversion unit. The contacting may include passing the olefin-rich hydrocarbon stream into and through an olefin interconversion unit in which the catalyst system is already present. The contacting may include passing a combined stream including the olefin-rich hydrocarbon stream and the catalyst system into and through the olefin interconversion unit, such that the combined stream is formed before entering the olefin interconversion unit.

According to some embodiments, the olefin interconversion unit may include a riser reactor or a downer reactor. As used in this disclosure, the term "downer" refers to a reactor, such as a fluidized bed reactor, where the reactant flows in a generally downward direction such as, for example, entering the top and exiting the bottom of the reactor. Likewise, the term "riser" refers to a reactor, such as a fluidized bed reactor, where the reactant flows in a generally upward direction such as, for example, entering the bottom and exiting the top of the reactor. According to some embodiments, the olefin interconversion unit is chosen from a fluidized bed reactor, a fixed-bed reactor, and a moving-bed reactor. According to some embodiments, the olefin-rich hydrocarbon stream may be an effluent from a steam pyrolysis unit or a fluidized catalytic cracking unit, any of which may include a riser, a downer, or both.

The olefin-rich hydrocarbon stream, which is the feed to the olefin interconversion unit, may be passed to the interconversion unit from any cracking unit, including naphtha crackers or FCC units. The olefin interconversion unit may be a stand-alone facility, an add-on apparatus, or a reactor fully integrated with a steam cracker. For a stand-alone unit, the product from the olefin interconversion unit may be fed to a separation section for propylene recovery, ethylene recovery, or both. For an integrated unit, the product from the olefin interconversion unit may be fed to a recovery section of the steam cracker. The exact feed points depend on the capacity of the columns and the separation scheme of a particular plant. Unreacted streams can be sent back to the selective olefin cracking unit for further conversion. Thus, in some embodiments, the methods for interconverting olefins in an olefin-rich hydrocarbon stream may further include recycling unconverted olefins back to the interconversion unit for extinction.

Olefin interconversion catalyzed by a catalyst system as described in this disclosure may be performed under ordinary conditions for olefin interconversion of an olefin-rich hydrocarbon stream. For example, the conditions described below can be suitably used. The catalyst system as previously described may be charged into a reactor vessel and suitably used for catalytic cracking of hydrocarbon oil according to known olefin interconversion processes for production of gasoline and/or light olefins including ethylene and propylene.

In example embodiments, the contacting of the olefin-rich hydrocarbon stream may be conducted in the olefin interconversion unit at a reaction temperature from 450° C. to 750° C., a reaction pressure from 1 bar to 5 bar, and a residence time from 0.5 seconds to 1000 seconds.

The methods for interconverting olefins in an olefin-rich hydrocarbon stream may further include selectively hydrogenating a raffinate stream containing diolefins to produce the olefin-rich hydrocarbon stream, before contacting the olefin-rich hydrocarbon stream with the catalyst system. In such embodiments, the raffinate stream may be any refinery stream containing diolefins that may be selectively hydrogenated to mono-olefins. Examples of such streams include raw C4 streams and hydrocarbon streams that contain 1,3-butadiene. By the selective hydrogenation, the olefin-rich hydrocarbon stream contains a lesser content of diolefins than the raffinate stream. Without intent to be bound by theory, it is believed that, by decreasing the concentration of diolefins in the olefin-rich hydrocarbon stream prior to olefin interconversion, hydrogen transfer reactions, cyclizations, and aromatizations can be decreased, minimized, or even eliminated, such that reactions leading to olefins such as ethylene and propylene can be heavily favored.

In the methods for interconverting olefins in an olefin-rich hydrocarbon stream, the contacting of the olefin-rich hydrocarbon stream with the catalyst system produces an interconverted effluent containing ethylene and propylene. It should be understood by the skilled person that the composition of the interconverted effluent depends heavily on the composition of the olefin-rich hydrocarbon stream prior to the interconversion reaction. It should be understood also by the skilled person that the interconverted effluent will contain hydrocarbons in addition to propylene and ethylene. In embodiments, the yields of propylene, ethylene, or both, when the catalyst system includes the framework-substituted *BEA-type catalyst as described in this disclosure are comparatively greater than the yields of propylene, ethylene, or both formed by interconversion in the presence of another known catalyst system. According to embodiments, the interconverted effluent may include greater than 1% by mass propylene, greater than 2% by mass propylene, greater than 5% by mass propylene, greater than 10% by mass propylene, greater than 20% by mass propylene, greater than 30% by mass propylene, greater than 40% by mass propylene, greater than 50% by mass propylene, from 1% to 60% by mass propylene, or even greater than 60% by mass propylene, based on the total mass of the interconverted effluent. According to embodiments, the interconverted effluent may include greater than 1% by mass ethylene, greater than 2% by mass ethylene, greater than 5% by mass ethylene, from 1% to 10% by mass ethylene, greater than 10% by mass ethylene, from 1% to 20% by mass ethylene, or even greater than 20% by mass ethylene, based on the total mass of the interconverted effluent.

EXAMPLES

The embodiments described in this disclosure will be better understood by reference to the following examples, which are offered by way of illustration and which one skilled in the art will recognize are not meant to be limiting.

A mid-cut naphtha stream was used as an olefin-rich hydrocarbon stream. The mid-cut naphtha stream was cracked in a FCC MAT unit at 550° C., 30 seconds of residence time, 1 bar of pressure, with a catalyst-to-oil mass ratio of 3.87. Selected properties of the mid-cut naphtha stream are provided in Table 1.

TABLE 1

Properties of mid-cut naphtha stream used as olefin-rich hydrocarbon stream in the present Example

| Property | Value | Distillation (D86) | |
|---|---|---|---|
| Density at 15 ° C. | 0.760 kg/L | Initial Boiling Point | 88° C. |
| Carbon | 86.26 wt. % | 10 wt.% | 99° C. |
| Hydrogen | 13.34 wt. % | 30 wt.% | 101° C. |
| Sulfur | <10 ppmw | 50 wt.% | 102° C. |
| Nitrogen | <10 ppmw | 70 wt.% | 120° C. |
| | | 90 wt.% | 132° C. |
| | | Final Boiling Point | 148° C. |

The composition of the mid-cut naphtha stream is provided in Table 2.

TABLE 2

Composition of mid-cut naphtha stream used as olefin-rich hydrocarbon stream in the present Example

| | Carbon Number | | | | | | | | |
|---|---|---|---|---|---|---|---|---|---|
| Component | 5 | 6 | 7 | 8 | 9 | 10 | 11 | 12 | Total |
| Aromatics | 0.00 | 0.84 | 8.24 | 15.82 | 2.04 | 0.00 | 0.00 | 0.00 | 26.94 |
| iso-Alkanes | 0.00 | 0.05 | 5.64 | 11.14 | 6.12 | 0.80 | 0.00 | 0.00 | 23.74 |
| Cycloalkanes | 0.00 | 2.67 | 12.89 | 9.29 | 1.29 | 0.00 | 0.00 | 0.00 | 26.14 |
| n-Alkanes | 0.00 | 0.44 | 1.41 | 1.52 | 0.54 | 0.00 | 0.00 | 0.00 | 3.90 |
| Olefins | 0.00 | 3.09 | 14.53 | 1.65 | 0.00 | 0.00 | 0.00 | 0.00 | 19.28 |
| Total | 0.00 | 7.10 | 42.70 | 39.41 | 9.99 | 0.80 | 0.00 | 0.00 | 100.00 |

For olefin interconversion, the mid-cut naphtha stream was contacted with a catalyst system including (Ti,Zr)-*BEA according to embodiments of this disclosure as the only zeolite catalyst. The product yields from the interconversion process are summarized in Table 3.

TABLE 3

Product yield from olefin interconversion of the mid-cut naphtha stream in the presence of (Ti,Zr)-*BEA catalyst

| # | Component | Yield (wt. %) |
|---|---|---|
| 1 | Hydrogen | 0.06 |
| 2 | Methane | 1.99 |
| 3 | Ethane | 1.8 |
| 4 | Ethylene | 2.41 |
| 5 | Propane | 22.95 |
| 6 | Propylene | 4.32 |
| 7 | i-Butane | 10.08 |
| 8 | n-Butane | 6.31 |
| 9 | trans-2-Butene | 0.66 |
| 10 | 1-Butene | 0.52 |
| 11 | iso-Butylene | 1.10 |
| 12 | cis-2-Butene | 0.00 |
| 13 | 1,3-Butadiene | 0.77 |
| 14 | Other C4 Olefins | 0.03 |
| Total Gas (sum of 1-14) | | 53.00 |
| 15 | Gasoline | 31.92 |

TABLE 3-continued

Product yield from olefin interconversion of the mid-cut naphtha stream in the presence of (Ti,Zr)-*BEA catalyst

| # | Component | Yield (wt. %) |
|---|---|---|
| 16 | LCO | 3.48 |
| 17 | HCO | 0.15 |
| 18 | Coke | 11.45 |
| TOTAL | | 100 |

As presented in Table 2, the total olefins present in the mid-cut naphtha feed stream were 19.28 wt. %. As presented in Table 4, the interconversion process produced a product stream containing 4.32 wt. % propylene and 2.41 wt. % ethylene. Thus, the framework-substituted beta zeolite catalyst according to embodiments of this disclosure is demonstrated as a suitable catalyst for producing propylene and ethylene from an olefin-rich hydrocarbon stream such as the mid-cut naphtha of the present Example.

Items Listing

Embodiments of the present disclosure include at least the following items, which are not intended to limit the scope of the disclosure as a whole or the appended claims.

Item 1: A method for interconverting olefins in an olefin-rich hydrocarbon stream, the method comprising: contacting the olefin-rich hydrocarbon stream with a catalyst system in an olefin interconversion unit to produce an interconverted effluent comprising ethylene and propylene, wherein the contacting is conducted at a reaction temperature from 450° C. to 750° C., a reaction pressure from 1 bar to 5 bar, and a residence time from 0.5 seconds to 1000 seconds, wherein: the catalyst system comprises a framework-substituted beta zeolite; and the framework-substituted beta zeolite has a modified *BEA framework, the modified *BEA framework comprising a *BEA aluminosilicate framework modified by substituting a portion of framework aluminum atoms of the *BEA aluminosilicate framework with beta-zeolite Al-substitution atoms independently selected from the group consisting of titanium atoms, zirconium atoms, and hafnium atoms.

Item 2: The method of Item 1, wherein the framework-substituted beta zeolite contains from 0.01% to 5% beta-zeolite Al-substitution atoms, as calculated on an oxide basis, based on the total mass of the framework-substituted beta zeolite.

Item 3: The method of Item 1 or Item 2, wherein: the framework-substituted beta zeolite contains from 0.01% to 5% by mass substitution atoms, as calculated on an oxide basis, based on the total mass of the framework-substituted beta zeolite; and the beta-zeolite Al-substitution atoms comprise a combination selected from the group consisting of (a) titanium atoms and zirconium atoms, (b) titanium atoms and hafnium atoms, (c) zirconium atoms and hafnium atoms, and (d) titanium atoms, zirconium atoms, and hafnium atoms.

Item 4: The method of any of Items 1 to 3, wherein: the framework-substituted beta zeolite contains from 0.01% to 5% beta-zeolite Al-substitution atoms, as calculated on an oxide basis, based on the total mass of the framework-substituted beta zeolite; and the beta-zeolite Al-substitution atoms comprise titanium atoms and zirconium atoms.

Item 5: The method of any of Items 1 to 4, wherein the framework-substituted beta zeolite has: (a) a specific surface area of 400 m$^2$/g to 800 m$^2$/g; (b) a molar ratio of $SiO_2$ to $Al_2O_3$ from 10 to 200; (c) a pore volume from 0.2 cm$^3$/g to 0.6 cm$^3$/g; and (d) crystal lattice constants a=1.26 nm to 1.27 nm, b=1.26 nm to 1.27 nm, and c=2.62 nm to 2.65 nm.

Item 6: The method of any of Items 1 to 5, wherein the framework-substituted beta zeolite has mesopores having diameters from 4 nm to 100 nm.

Item 7: The method of any of Items 1 to 6, wherein the catalyst system comprises from 2% to 90% by mass framework-substituted beta zeolite, based on the total mass of the catalyst system.

Item 8: The method of any of Items 1 to 7, wherein the olefin-rich hydrocarbon stream comprises hydrocarbons having from 4 to 12 carbon atoms.

Item 9: The method of any of Items 1 to 8, wherein the olefin-rich hydrocarbon stream is an effluent from a steam pyrolysis unit or a fluidized catalytic cracking unit.

Item 10: The method of any of Items 1 to 9, wherein the catalyst system further comprises a binder chosen from amorphous silica-alumina and alumina.

Item 11: The method of any of Items 1 to 10, wherein the binder is amorphous silica-alumina and the olefin-rich hydrocarbon stream is an effluent from a steam pyrolysis unit or a fluidized catalytic cracking unit.

Item 12: The method of any of Items 1 to 11, wherein the catalyst system further comprises a framework-substituted ultra-stable Y-zeolite.

Item 13: The method of Item 12, wherein the framework-substituted USY-zeolite has a modified USY framework, the modified USY framework comprising a USY aluminosilicate framework modified by substituting a portion of framework aluminum atoms of the USY aluminosilicate framework with USY-zeolite Al-substitution atoms independently selected from the group consisting of titanium atoms, zirconium atoms, hafnium atoms, and combinations thereof.

Item 14: The method of Item 12 or Item 13, wherein the framework-substituted ultra-stable Y-zeolite contains from 0.01% to 5% USY-zeolite Al-substitution atoms, as calculated on an oxide basis, based on the total mass of the framework-substituted ultra-stable Y-zeolite.

Item 15: The method of any of Items 12 to 14, wherein the framework-substituted ultra-stable Y-type zeolite has: (a) crystal lattice constants a and b from 2.43 nm to 2.45 nm; (b) a specific surface area from 600 m$^2$/g to 900 m$^2$/g; and (c) a molar ratio of $SiO_2$ to $Al_2O_3$ from 5:1 to 100:1.

Item 16: The method of any of Items 12 to 15, wherein: the framework-substituted beta zeolite contains from 0.01% to 5% beta-zeolite Al-substitution atoms, as calculated on an oxide basis, based on the total mass of the framework-substituted beta zeolite; the beta-zeolite Al-substitution atoms comprise titanium atoms and zirconium atoms; the framework-substituted ultra-stable Y-zeolite contains from 0.01% to 5% USY-zeolite Al-substitution atoms, as calculated on an oxide basis, based on the total mass of the framework-substituted ultra-stable Y-zeolite; and the USY-zeolite Al-substitution atoms comprise titanium atoms and zirconium atoms.

Item 17: The method of any of Items 1 to 16, further comprising: before contacting an olefin-rich hydrocarbon stream with a catalyst system, selectively hydrogenating a raffinate stream containing diolefins to produce the olefin-rich hydrocarbon stream, whereby the olefin-rich hydrocarbon stream contains a lesser content of diolefins than the raffinate stream.

Item 18: The method of any of Items 1 to 17, further comprising: recycling unconverted olefins back to the reactor for extinction.

Item 19: The method of any of Items 1 to 18, wherein the olefin-rich hydrocarbon stream is selected from a raw C4 stream, a raffinate-1 stream, a raffinate-2 from a steam cracker, a C4 stream from a fluid catalytic cracker, and a C5+ stream from cracker pyrolysis gasoline.

Item 20: The method of any of Items 1 to 19, wherein the olefin interconversion unit is chosen from a fluidized bed reactor, a fixed-bed reactor, and a moving-bed reactor.

Item 21: The method of any of Items 1 to 20, wherein the framework-substituted *BEA-type zeolite catalyst additive is a (Ti,Zr)-*BEA zeolite having (a) a specific surface area of 400 m$^2$/g to 800 m$^2$/g; (b) a molar ratio of $SiO_2$ to $Al_2O_3$ of about 60; (c) a pore volume from 0.38 cm$^3$/g to 0.43 cm$^3$/g; and (d) crystal lattice constants a=1.26 nm to 1.27 nm, b=1.26 nm to 1.27 nm, and c=2.62 to 2.65 nm.

Unless otherwise defined, all technical and scientific terms used herein have the same meaning as commonly understood by one of ordinary skill in the art to which the invention belongs. The terminology used in the description herein is for describing particular embodiments only and is not intended to be limiting. As used in the specification and appended claims, the singular forms "a," "an," and "the" are intended to include the plural forms as well, unless the context clearly indicates otherwise.

For the purposes of describing and defining the present disclosure it is noted that the term "about" is utilized herein to represent the inherent degree of uncertainty that may be attributed to any quantitative comparison, value, measurement, or other representation. The term "about" is also utilized herein to represent the degree by which a quantitative representation may vary from a stated reference without resulting in a change in the basic function of the subject matter at issue.

It is noted that one or more of the following claims utilize the term "wherein" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising."

It should be understood that any two quantitative values assigned to a property may constitute a range of that property, and all combinations of ranges formed from all stated quantitative values of a given property are contemplated herein.

While particular embodiments have been illustrated and described herein, it should be understood that various other changes and modifications may be made without departing from the scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A method for interconverting olefins in an olefin-rich hydrocarbon stream, the method comprising:
contacting the olefin-rich hydrocarbon stream with a catalyst system in an olefin interconversion unit to produce an interconverted effluent comprising ethylene and propylene, wherein the contacting is conducted at a reaction temperature from 450° C. to 750° C., a reaction pressure from 1 bar to 5 bar, and a residence time from 0.5 seconds to 1000 seconds,
wherein:
the olefin-rich hydrocarbon stream is a hydrocarbon stream containing at least 20% by mass olefins, based on the total mass of the hydrocarbon stream;
the catalyst system comprises a framework-substituted beta zeolite; and
the framework-substituted beta zeolite has a modified *BEA framework, the modified *BEA framework comprising a *BEA aluminosilicate framework modified by substituting a portion of framework aluminum atoms of the *BEA aluminosilicate framework with beta-zeolite Al-substitution atoms independently selected from the group consisting of titanium atoms, zirconium atoms, and hafnium atoms.

2. The method of claim 1, wherein the framework-substituted beta zeolite contains from 0.01% to 5% beta-zeolite Al-substitution atoms, as calculated on an oxide basis, based on the total mass of the framework-substituted beta zeolite.

3. The method of claim 1, wherein:
the framework-substituted beta zeolite contains from 0.01% to 5% by mass substitution atoms, as calculated on an oxide basis, based on the total mass of the framework-substituted beta zeolite; and
the beta-zeolite Al-substitution atoms comprise a combination selected from the group consisting of (a) titanium atoms and zirconium atoms, (b) titanium atoms and hafnium atoms, (c) zirconium atoms and hafnium atoms, and (d) titanium atoms, zirconium atoms, and hafnium atoms.

4. The method of claim 1, wherein:
the framework-substituted beta zeolite contains from 0.01% to 5% beta-zeolite Al-substitution atoms, as calculated on an oxide basis, based on the total mass of the framework-substituted beta zeolite; and
the beta-zeolite Al-substitution atoms comprise titanium atoms and zirconium atoms.

5. The method of claim 1, wherein the framework-substituted beta zeolite has:
(a) a specific surface area of 400 $m^2/g$ to 800 $m^2/g$;
(b) a molar ratio of $SiO_2$ to $Al_2O_3$ from 10 to 200;
(c) a pore volume from 0.2 $cm^3/g$ to 0.6 $cm^3/g$; and
(d) crystal lattice constants a=1.26 nm to 1.27 nm, b=1.26 nm to 1.27 nm, and c=2.62 nm to 2.65 nm.

6. The method of claim 1, wherein the catalyst system comprises from 2% to 90% by mass framework-substituted beta zeolite, based on the total mass of the catalyst system.

7. The method of claim 1, wherein the olefin-rich hydrocarbon stream comprises hydrocarbons having from 4 to 12 carbon atoms.

8. The method of claim 1, wherein the olefin-rich hydrocarbon stream is an effluent from a steam pyrolysis unit or a fluidized catalytic cracking unit.

9. The method of claim 1, wherein the catalyst system further comprises a binder chosen from amorphous silica-alumina and alumina.

10. The method of claim 9, wherein the binder is amorphous silica-alumina and the olefin-rich hydrocarbon stream is an effluent from a steam pyrolysis unit or a fluidized catalytic cracking unit.

11. The method of claim 1, wherein the catalyst system further comprises a framework-substituted ultra-stable Y-zeolite.

12. The method of claim 11, wherein the framework-substituted USY-zeolite has a modified USY framework, the modified USY framework comprising a USY aluminosilicate framework modified by substituting a portion of framework aluminum atoms of the USY aluminosilicate framework with USY-zeolite Al-substitution atoms independently selected from the group consisting of titanium atoms, zirconium atoms, hafnium atoms, and combinations thereof.

13. The method of claim 12, wherein the framework-substituted ultra-stable Y-zeolite contains from 0.01% to 5% USY-zeolite Al-substitution atoms, as calculated on an oxide basis, based on the total mass of the framework-substituted ultra-stable Y-zeolite.

14. The method of claim 12, wherein the framework-substituted ultra-stable Y-type zeolite has:
(a) crystal lattice constants a and b from 2.43 nm to 2.45 nm;
(b) a specific surface area from 600 $m^2/g$ to 900 $m^2/g$; and
(c) a molar ratio of $SiO_2$ to $Al_2O_3$ from 5:1 to 100:1.

15. The method of claim 11, wherein:
the framework-substituted beta zeolite contains from 0.01% to 5% beta-zeolite Al-substitution atoms, as calculated on an oxide basis, based on the total mass of the framework-substituted beta zeolite;
the beta-zeolite Al-substitution atoms comprise titanium atoms and zirconium atoms;
the framework-substituted ultra-stable Y-zeolite contains from 0.01% to 5% USY-zeolite Al-substitution atoms, as calculated on an oxide basis, based on the total mass of the framework-substituted ultra-stable Y-zeolite; and
the USY-zeolite Al-substitution atoms comprise titanium atoms and zirconium atoms.

16. The method of claim 1, further comprising:
before contacting an olefin-rich hydrocarbon stream with a catalyst system, selectively hydrogenating a raffinate stream containing diolefins to produce the olefin-rich hydrocarbon stream, whereby the olefin-rich hydrocarbon stream contains a lesser content of diolefins than the raffinate stream.

17. The method of claim 1, further comprising:
recycling unconverted olefins back to the reactor for extinction.

18. The method of claim 1, wherein the olefin-rich hydrocarbon stream is selected from a raw C4 stream, a raffinate-1 stream, a raffinate-2 from a steam cracker, a C4 stream from a fluid catalytic cracker, and a C5+ stream from cracker pyrolysis gasoline.

19. The method of claim 1, wherein the olefin interconversion unit is chosen from a fluidized bed reactor, a fixed-bed reactor, and a moving-bed reactor.

* * * * *